United States Patent [19]

Porter et al.

[11] Patent Number: 5,284,480
[45] Date of Patent: Feb. 8, 1994

[54] INFLATION/DEFLATION SYRINGE WITH THREADED PLUNGER

[75] Inventors: William M. Porter, Carlsbad; Susan L. Stout, Del Mar, both of Calif.

[73] Assignee: Medtronic, Inc., Minneapolis, Minn.

[21] Appl. No.: 8,049

[22] Filed: Jan. 22, 1993

Related U.S. Application Data

[63] Continuation of Ser. No. 612,043, Nov. 9, 1990, abandoned.

[51] Int. Cl.$^5$ .............................................. A61M 29/00
[52] U.S. Cl. ........................................ 604/97; 604/99; 604/211; 604/224
[58] Field of Search .............................. 604/97–100, 604/118, 121, 208, 209, 211, 218, 224; 222/638, 639; 73/715, 730, 732, 741, 706

[56] References Cited

U.S. PATENT DOCUMENTS

| | | | |
|---|---|---|---|
| 2,568,238 | 10/1951 | Le Van | 73/732 |
| 3,496,776 | 2/1970 | Mistarz | 73/741 |
| 3,818,903 | 6/1974 | Bleecker | 128/349 |
| 4,184,375 | 1/1980 | Gray | 73/706 |
| 4,205,683 | 6/1980 | O'Neill | 128/348 |
| 4,297,891 | 11/1981 | Falcon | 73/706 |
| 4,370,982 | 2/1983 | Reilly | 604/98 |
| 4,476,866 | 10/1984 | Chin | 128/344 |
| 4,535,757 | 8/1985 | Webster, jr. | 128/1 |
| 4,583,974 | 4/1986 | Kokernak | 604/211 |
| 4,641,533 | 2/1987 | Mueller et al. | 73/732 |
| 4,655,749 | 4/1987 | Fischione | 604/98 |
| 4,658,829 | 4/1987 | Wallace | 128/748 |
| 4,723,938 | 2/1988 | Goodin et al. | 604/99 |
| 4,740,203 | 4/1988 | Hoskins et al. | 604/191 |
| 4,743,230 | 5/1988 | Nordquest | 604/98 |
| 4,758,223 | 7/1988 | Rydell | 604/98 |
| 4,790,821 | 12/1988 | Stines | 604/100 |
| 4,795,431 | 1/1989 | Walling | 604/97 |
| 4,808,165 | 2/1989 | Carr | 604/97 |
| 4,810,249 | 3/1989 | Haber et al. | 604/211 |
| 4,832,692 | 5/1989 | Box et al. | 604/99 |
| 4,838,864 | 6/1989 | Peterson et al. | 604/100 |
| 4,865,587 | 9/1989 | Walling | 604/97 |
| 4,919,121 | 4/1990 | Rydell et al. | 604/97 |
| 4,929,238 | 5/1990 | Baum | 604/208 |
| 4,940,459 | 7/1990 | Noce | 604/98 |
| 5,000,049 | 3/1991 | Cooper et al. | 73/741 |
| 5,019,041 | 5/1991 | Robinson et al. | 604/211 |
| 5,021,046 | 6/1991 | Wallace | 604/100 |
| 5,168,757 | 12/1992 | Rabenau et al. | 604/99 |

*Primary Examiner*—John D. Yasko
*Assistant Examiner*—Anthony Gutowski
*Attorney, Agent, or Firm*—Dianne M. F. Plunkett; Harold R. Patton

[57] ABSTRACT

An inflation device is disclosed for inflation of a balloon of a balloon catheter. A housing defines a fluid-receiving reservoir in fluid communication with the balloon and an interior space for completely receiving a pressure gauge which accesses the fluid for measurement of the pressure within the system.

The reservoir has a piston and threaded plunger extending from a proximal opening in the reservoir. The threaded plunger is selectively engaged by a biased rotatable arm on the housing. The piston and plunger are part of a syringe received within the reservoir, and the housing defines an aperture for visual readout of the level of liquid in the reservoir.

The pressure gauge contains a Bourdon tube and further contains a gauge fluid in communication with the tube. The means for isolating the inflation fluid from the gauge is an expandable bladder disposed in the neck between the gauge and the inflation fluid so that the bladder expands upon increased fluid pressure within the closed system to create a pressure readout.

The housing defines an aperture for visual readout of a timer in the form of an LCD display with a frontally-illuminated screen. The timer has a manual activation lever and the housing includes an aperture allowing manual activation of the lever.

9 Claims, 3 Drawing Sheets

INFLATION/DEFLATION SYRINGE WITH THREADED PLUNGER

This is a continuation of application Ser. No. 07/612,043, filed Nov. 9, 1990, (abandoned).

BACKGROUND OF THE INVENTION

1. Field of the Invention

This invention relates to devices for inflating balloons or the like, particularly medical devices for inflating the balloons of catheters.

2. Description of the Prior Art

Many catheters currently in use in the vascular system have balloons located at their distal end. Angioplasty catheters, for example, have such balloons which are inflated within a plaque-containing stenosis to reform the stenosis to conform to the artery wall.

Angioplasty procedures can be painful to the patient if inflation lasts a long time so separate stopwatches which require separate handling are now frequently used in conjunction with the catheter to measure the length of inflation.

Special devices for inflating the balloon with a liquid such as saline or contrast media are also well known in the art. Originally, syringes were used for this purpose, and more sophisticated syringe-containing inflation devices have recently developed.

In order to control the amount of liquid (usually contrast media) injected into the balloon and obtain optimum inflation without balloon rupture, it has been found advisable to control the pressure input to the balloon. Devices which limit the amount of pressure in the inflation are disclosed in U.S. Pat. Nos. 4,795,431 and 4,865,587, both issued to Walling. Devices containing apparently removable pressure gauges external to the housing are shown in U.S. Pat. Nos. 4,743,230, 4,723,938, 4,758,223, and 4,919,121 issued to Nordquest, Goodin, Rydell and Rydell. However, it is highly desirable to include the pressure gauge in one, disposable unit with the inflation device, for convenience of the user, and avoid lengthy set-up procedures and the ordering of multiple devices.

Typical pressure gauges currently used with inflation devices are gauges based on Bourdon tubes. A Bourdon tube, somewhat flexible, and empty of liquid in the absence of a pressure reading, accesses a fluid-containing neck in the gauge which in turn accesses the channel in the inflation device delivering contrast media to the catheter. Upon pressure buildup, contrast media fills the neck and the tube, and compressing the air in the tube to change the tube's position so that a lever attached at the far end adjusts the position of the pressure gauge pointer. In the process, the contrast media in contact with the gauge, in particular the lead in the solder, becomes discolored and may well be toxic, such that a rupture in the balloon which leaks contrast media into the vasculature is potentially dangerous.

Using an externally-located, reusable (rather than disposable) pressure gauge and attempting to solve a different problem, i.e, the necessity of resterilizing an inflation device before re-use because the contrast media has come in contact with an external unsterilized pressure gauge, Reilly, in U.S. Pat. No. 4,370,982, discloses a multi-barrel inflation device attached to an external pressure gauge in which pressure measurement is based on axial movement of a barrel relative to the housing rather than direct pressure of the inflation fluid on the pressure gauge. It thus isolates the inflation fluid from the pressure gauge. The device, however, is complex, having a number of moving parts and an external pressure gauge, and thus may be expensive and cumbersome to manufacture and requires assembly with the pressure gauge before use.

According to Reilly in the Background of the Invention section of U.S. Pat. No. 4,370,982, it was previously known to interpose a T-fitting between the syringe of the inflation device and the catheter by interposing a gauge using a "separate pressure sensing member or disposable diaphragm positioned between the delivery end of the syringe and the balloon. One end of the diaphragm is contacted by the media fluid entering the balloon. While not admitting that this disclosure is enabling, it appears clear that a separate, disposable diaphragm (i.e. a disk) would have been used to separate the gauge from the fluid. In addition, the use of both a separate, nondisposable pressure gauge and the separate disposable diaphragm would have required special parts and special assembly of the device prior to use.

It thus would be desirable to provide a single-unit, already assembled, inflation device which avoids inflation fluid contamination by the pressure gauge. It would further be desirable to provide an inflation device which can be conveniently handled with a timer such as a stopwatch.

SUMMARY OF THE INVENTION

In one aspect, the invention is a device for inflation of an expandable member of a closed system, such as the balloon of a balloon catheter, which includes a housing completely receiving a pressure gauge and means for isolating the inflation fluid, usually a biocompatible liquid, from the interior of the gauge. Specifically, a housing defines a liquid-receiving reservoir in fluid communication with the closed system and an interior space for completely receiving the pressure gauge which accesses the fluid for measurement of the fluid pressure. Means for ejecting fluid from the reservoir into the closed system is included.

Usually, the pressure gauge is a gauge having a face for pressure readout, a neck containing a silicone fluid, a movable unit accessing the neck, and a lever attached to the movable unit to actuate the readout of the gauge upon movement of the unit, and the user receives the pressure readout via an aperture in the housing for the face of the gauge. Usually the gauge is a Bourdon gauge or the like.

In the preferred embodiment, the means for isolating is an expandable bladder disposed in the neck of the gauge between the gauge and the fluid so that the bladder expands into the neck upon increased fluid pressure within the closed system to force the silicone fluid into the tube for a pressure readout.

Generally, the reservoir has distal and proximal ports and the means for ejecting is a piston movable in the reservoir via a plunger attached to the proximal end of the piston and extending out through the proximal port of the reservoir. The piston and plunger are usually part of a syringe received within the reservoir, and the housing defines a window for easy reading of the piston position and amount of liquid in the syringe.

In another aspect of the invention, the housing receives a timer for convenient timing of inflation. Usually, the timer is a stopwatch and the housing defines an aperture for the stopwatch's display. This is in the form of a liquid crystal display with a frontally-illuminated screen. The timer usually has a manual clock activation-/inactivation means and manual on/off means for the light. The housing includes apertures allowing activation of said means.

The invention in another aspect includes a method of inflating a balloon of a balloon catheter without contaminating the inflation fluid. The method includes providing a housing defining a reservoir receiving a blood-compatible inflation liquid, the reservoir being in fluid communication with the balloon and the housing further defining an interior space for completely receiving a pressure gauge for measurement of the pressure in the catheter. It further includes ejecting fluid from the reservoir into the closed system, and isolating the fluid from the interior of the pressure gauge to avoid contamination of the fluid.

The step of isolating can include the steps of providing a pressure gauge with a neck containing a gauge fluid, a unit accessing the neck and movable in response to the gauge fluid, and a lever attached to the movable unit for actuating readout of the pressure on the gauge as the unit moves; providing a bladder disposed between the fluid and the gauge in the neck; and expanding the bladder in response to increased inflation fluid pressure in the system so that the gauge fluid moves the unit to cause a pressure readout in response to the fluid pressure.

The step of ejecting is usually accomplished by providing a piston attached to a plunger which extends out through the proximal end of the reservoir, and moving the plunger proximally with respect to the reservoir for ejection of the fluid into the balloon.

Also usually included is the step of timing the inflation by activating a timer received within the housing, and receiving a readout of the inflation time.

DETAILED DESCRIPTION OF THE SPECIFIC EMBODIMENTS

Figure 1:
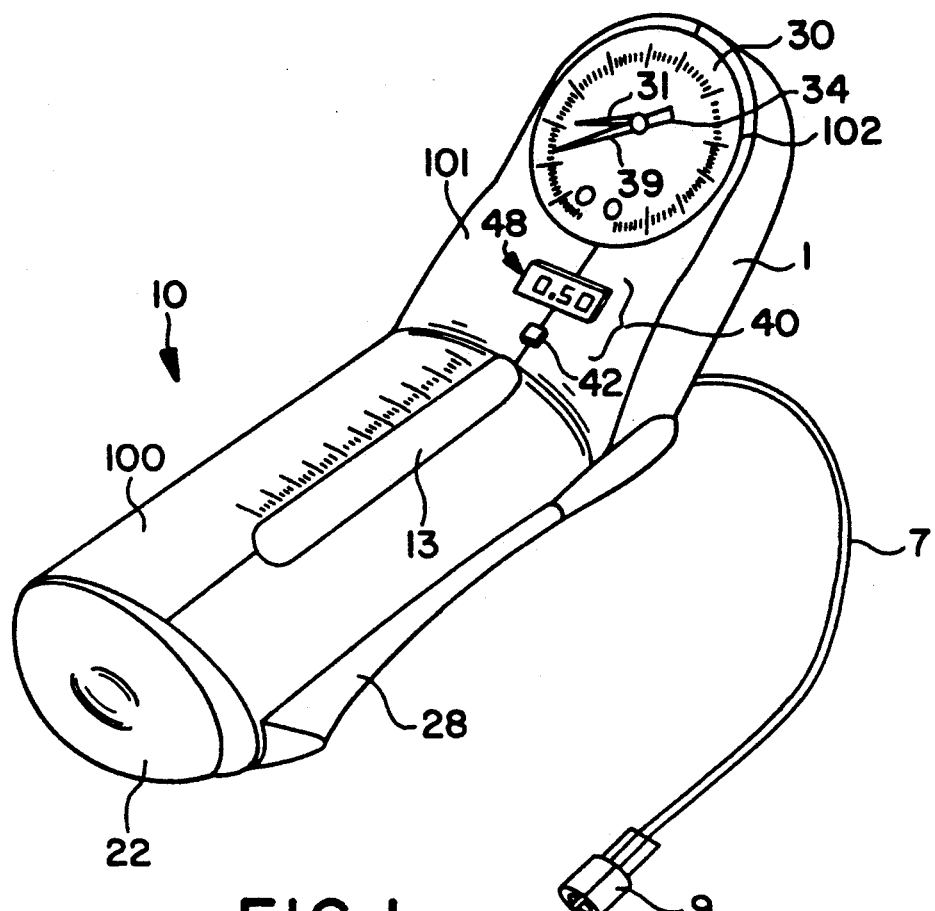
FIG. 1 is a perspective view of an embodiment of the inflation device of the present invention attached to the inflation port of an angioplasty catheter, as used in operation.

Referring to FIG. 1, an overall view of an embodiment of the inflation device 10 of the present invention can be seen. The device includes a housing 1 having a longitudinal portion 100 and an upwardly angled portion 101 at a 45° angle. The longitudinal portion defines an axially-extending longitudinal reservoir 3 which contains a syringe 104, 20 cc in volume, holding the inflation fluid, usually contrast media.

Tubing 7 and fitting 9 are in fluid communication with the distal port of the reservoir for attachment to the inflation port 13 of angioplasty catheter 11 for inflation of the catheter balloon during angioplasty. Although use with an angioplasty catheter is contemplated, the device of the present invention is equally at ease inflating the balloons of other catheters or inflating completely different devices.

Tubing 7 is sealingly attached at its proximal end to coupling elbow 5, around port 6 on the coupling elbow. Fitting 9 is designed for attachment to the inflation port of the catheter and is a swivel luer fitting in the preferred embodiment. Tubing 7 is preferably formed of a high pressure braided polyurethane. Coupling elbow 5 received within housing 1 provides fluid communication between tubing 7 and reservoir 3, and is preferably made of a stiff polymer, such as polycarbonate. Housing 1 is also generally formed of a stiff polymer, preferably polycarbonate.

Figure 2:
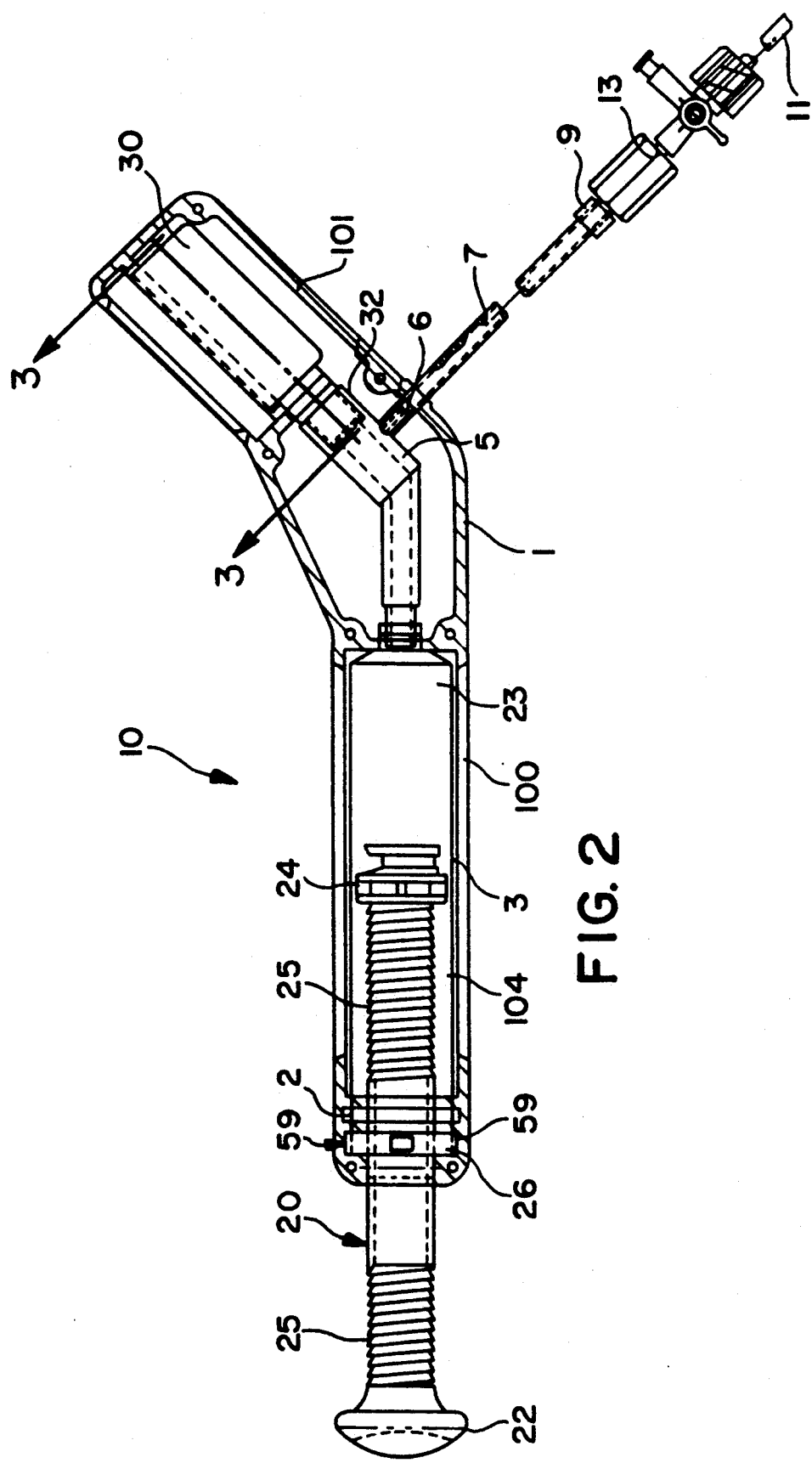
FIG. 2 is a side elevation in cross-section of an embodiment of the inflation device of the present invention.

As shown in FIG. 2, syringe 104 is usually formed of a moderately stiff polymer such as polypropylene. The preferred syringe is a commercially-available 20 cc unit made by Becton Dickinson.

Plunger 20 of syringe 104 is engaged by the user via external knob 22 located at its proximal end. Plunger 20 is seated within barrel 23 of syringe 104 in reservoir 3 and piston 24 is located at the distal end of plunger 20.

Piston 24 is larger in diameter than plunger 20 and is also larger in diameter than proximal entrance 2 to the syringe so as to prevent complete removal of the plunger from the device when it is withdrawn to its proximal extreme. Piston 24 is also slidable but sealingly received within barrel 23 to force contrast media in the reservoir distally through the reservoir, and out through coupling elbow 5, tubing 7, and fitting 9 into the catheter for inflation of the balloon, when the plunger is moved distally. Window gauge 13 longitudinally extending through the housing allows the user to view the syringe and the position of the plunger and/or contrast media to determine the amount of media left in the syringe.

Figure 4:
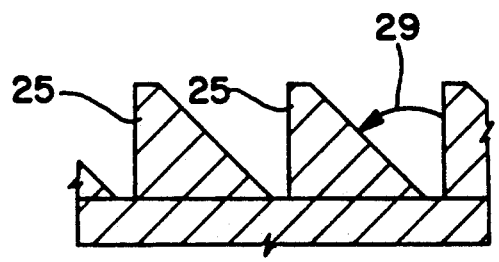
FIG. 4 is a fragmentary view, greatly enlarged, of the buttress threads circumferential to the plunger barrel of the present invention.

The circumference of plunger 20, generally cylindrical in cross-section, is formed of buttress threads 25, formed at a 45 degree angle (shown as 29 in FIG. 4) from the longitudinal or radial axis of the plunger, and are slightly spaced apart.

Figure 5A:
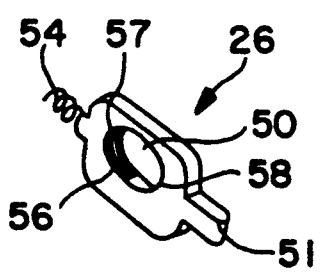
FIG. 5A and 5B are views of the thread engagement mechanism and engagement lever, respectively, in the device of the present invention.
Figure 5B:
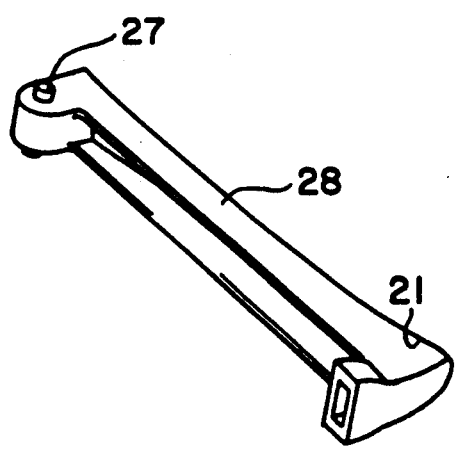

Longitudinally-extending clutch engagement lever 28 is shown in detail in FIG. 5B. It is attached to housing 1 at the distal end by pivot 27 attached to the housing, and about which the clutch revolves. The proximal end 21 of clutch 28 is attached to and receives lip 51 of thread engagement mechanism 26, a half nut, which extends through reservoir 3 and receives plunger 20.

Thread engagement means 26 is shown in FIG. 2 and specifically in FIG. 5A. It is located within reservoir 3, moves relative to reservoir 3 in slots 59 of housing 1, and defines an aperture 50, an elongated diametral with two centerpoints, the diameter sized to receive plunger 20. Lip 51 of mechanism 26 is attached to the proximal and innermost end of clutch engagement lever 28. The circumference 56 of aperture 50 on the side opposite to clutch 28 defines threads 57 complementary to buttress threads 25; the circumference 58 of aperture 50 adjacent to clutch 28 defines no threads.

Spring compression member 54 is attached at one end to the thread engagement mechanism opposite to clutch 28 and at the other end to housing 1 to provide resistance to inward movement of the proximal end of the clutch and to bias the engagement mechanism so that the plunger threads and engagement threads are in mating position unless clutch 28 is pressed inwardly, i.e., engaged.

Thus, in resting position, the piston can be moved forward only gradually and only by rotating the plunger. However, when the clutch is engaged, i.e pressed inward by the user, thread engagement mechanism 26 is repositioned in slots 59 so that the plunger is received within the non-threaded portion 58 of aperture 50, allowing smooth and rapid plunger movement directly forward and backwards without rotation. Release of clutch 28 and the outward urging of spring 54 relocks the plunger in place by mating the complementary and buttress threads. Both the clutch and the engagement mechanism are preferably formed of black polycarbonate.

Figure 3:
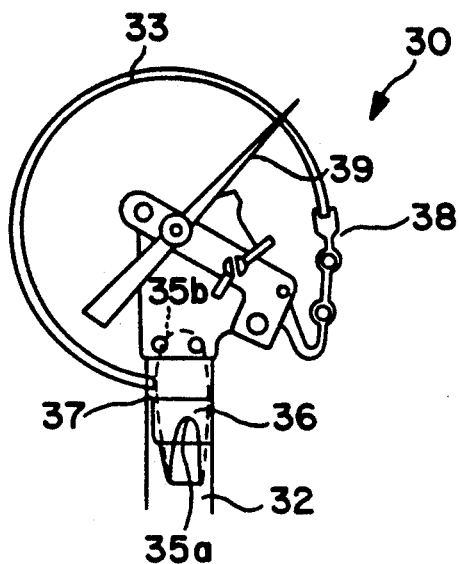
FIG. 3 is a frontal cross-section of a Bourdon pressure gauge and the bladder used in the present invention to isolate the fluid from the gauge, taken at lines 3—3 of FIG. 2.

A modified pressure gauge 30 having a Bourdon tube is disposed in the upwardly angled portion 101 of the housing. The housing defines a aperture 102 in the upward surface thereof to house the face 34 of the pressure gauge for convenient reading by the user. The gauge, insofar as it is standard, includes a neck 36 which is inserted into the upper end 32 of coupled elbow 5 as shown in FIG. 3. Tube 33 is attached to and accesses the neck. The tip of tube 33 is attached to lever linkage 38 attached in turn to pressure gauge pointer 39 and lazy needle 31 (not shown on FIG. 3)

In the prior art, during inflation, contrast media extends into neck 36, then into tube 33 and compressing the air within the tube to change the tube's position, causing linkage 38 to adjust pressure pointer 39 and lazy needle 31 to reflect current fluid pressure in the system. (Pressure pointer 39 normally reflects both increases and decreases in pressure while lazy needle 31 remains in place to record the highest inflation pressure during the procedure.)

The present device, however, includes bladder 35 made of EDPM (a terpolymer of ethylene propylene with a diene side chain) disposed in neck 36 and extending between the neck and fluid channel 32 to prevent the contrast media from coming in contact with the interior of the pressure gauge, and thereby becoming contaminated or possibly toxic. Silicone fluid is contained in the now-enclosed neck. Bladder 35 is shown unextended in position 35a and expanded in position 35b. Expansion causes the bladder 35 to force the silicone into tube 33, resulting in a pressure readout proportional to the pressure in the system. It has been found that the pressure readout caused by the bladder is in the range of about ±4 percent, whereas direct pressure readout is in the range of about ±2 or 3 percent.

Figure 6:
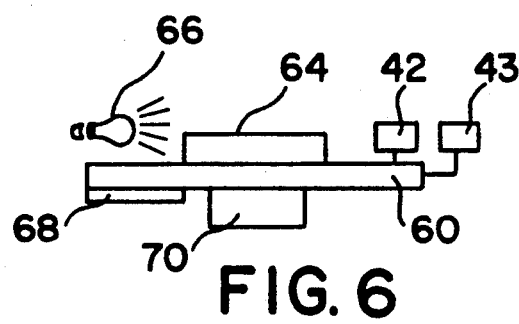
FIG. 6 is a schematic of the liquid crystal display and timer of the present invention.

A stopwatch 40 is included for convenient timing of inflation to provide the user with an indication of the amount of time the flow of blood has been blocked by balloon inflation and to generally provide information which would indicate a problem with inflation. Button 42, conventionally wired to a clock and readout, is used to initiate and end timing. Display 48 consists of liquid crystal letters on a frontally-illuminated screen constructed in a conventional manner. The entire timer is constructed in a conventional manner, using conventional, commercially-available components. In the preferred embodiment, LCD and frontally-illuminated display are made as shown in the schematic in FIG. 6.

A printed circuit board 60 is used which runs the clock 68, takes power from the photocell 70 and provides an on/off clock reset mechanism in response to activation of button 42 wired to the board. A light source 66 is placed directly above the board and the display 64. Light is transmitted to provide frontal illumination of the display. The timer or clock 68 and the photocell 70 are placed beneath the printed circuit board. The manual activation button 42 starts and stops the timer which is run by the board via energy provided by the battery. The light on/off button 43 turns on the light source and provides illumination to the display. The board then energizes the liquid crystal, energy-dependent, readout.

Before use, the fitting 9 is usually placed in saline solution or contrast media, the clutch engaged, and the plunger withdrawn to proximal position to prime the device.

The balloon is usually tested for inflation problems at this time, and the timing for inflation is noted. Plunger 20 is then pushed via knob 22 to its distal-most position to, clutch engaged, to eject the fluid, and contrast media is then drawn in.

For actual use, fitting 9 is securely attached to inflation port 13 of balloon catheter 11, which has been threaded over a guidewire into position in the vasculature for angioplasty or other purposes. Plunger 20 is moved proximally while clutch 28 is engaged by pressing inwardly on its proximal end and the stopwatch is activated.

As the balloon inflates, the window gauge in the reservoir shows decreasing amounts of contrast media in the reservoir, and the pressure gauge shows pressure increases. As the balloon appears to be nearly inflated, clutch 28 is disengaged by releasing the inward pressure on it, and forward movement of the plunger is activation by rotation. The amount of contrast media left in the reservoir can be read on the reservoir gauge 13, the pressure read on the pressure gauge, and the inflation time on the stopwatch.

Balloon deflation is accomplished by rotation of the plunger or by merely disengaging the clutch and directly withdrawing the plunger. For angioplasty or other procedures requiring repeated inflation and deflation, the insertion and removal of contrast media is repeated. After final deflation, the device can be removed from the catheter before the catheter is withdrawn from the vascular system. The lazy needle on the pressure gauge will reflect the maximum pressure used in each inflation cycle. It can then be manually reset to zero.

It will be understood that the above description and the illustrations are provided by way of example only, that alternate versions, equivalents, and examples will be apparent to those skilled in the art, and will be within the scope of the invention which is defined by the appended claims.

What is claimed is:

1. A device for inflating the balloon of a balloon catheter comprising:
   a longitudinally-extending housing defining a fluid-receiving reservoir and having a proximal and a distal end,
   means for connecting the housing to the catheter so that the reservoir is in fluid communication with the balloon of the catheter;
   a piston movable within the reservoir to eject fluid from the reservoir into the catheter;
   a plunger attached to the proximal end of the piston, the plunger having a threaded portion;

threaded means for engaging the threaded portion of the plunger, said means moveable between an engaged and a disengaged position;

an arm having a proximal and distal end and extending longitudinally with respect to the housing, said arm rotatably attached to the housing at its distal end and attached to the threaded means at the proximal end, so that movement of the proximal end of the arm moves the threaded means between an engaged and a disengaged position; and a biasing means for biasing the threaded means into engaged position.

2. A device according to claim 1 and wherein the threaded means includes buttress threads.

3. A device according to claim 2 and wherein the housing contains a pressure gauge for measuring the fluid pressure in the catheter.

4. A device according to claim 3 wherein the pressure gauge is a bourdon-type pressure gauge received within the housing and having a neck, the entrance to which accesses the fluid for pressure measurement, the device further comprising:

a liquid contained within the pressure gauge and neck so that the gauge reflects the pressure on the liquid; and an elastomer bladder sealed around the entrance to the neck so as to isolate the liquid from the fluid within the reservoir and exert pressure upon the liquid in response to pressure from the fluid to actuate the gauge, the bladder in shape of bubble disposed within the neck at rest and extending further within the neck under pressure.

5. A device according to claim 1 and wherein the housing contains a timer.

6. A device for inflating the balloon of a balloon catheter comprising:

a housing defining a fluid-receiving reservoir;

means for connecting the housing to the catheter so that the reservoir is in fluid communication with the balloon of the catheter;

a piston movable within the reservoir to eject fluid from the reservoir into the catheter;

a plunger attached to the proximal end of the piston, the plunger defining buttress threads;

threaded means for engaging the plunger, said means having buttress threads complementary to the buttress threads of the plunger and movable between an engaged and a disengaged position;

means for moving the threaded means between an engaged and a disengaged position;

wherein the means for moving the threaded portion is an arm rotatably attached to the housing at its distal end, the arm attached to the threaded means at its proximal end and adapted for transverse movement with respect to the plunger so that movement of the arm engages or disengages the threaded means; and a biasing means for biasing the arm into engaged position.

7. A device according to claim 7 and wherein the housing contains a pressure gauge for measuring the fluid pressure in the catheter.

8. A device according to claim 7 and wherein the pressure gauge is a bourdon-type pressure gauge received within the housing and having a neck, the entrance to which accesses the fluid for pressure measurement, the device further comprising:

a liquid contained within the pressure gauge and neck so that the gauge reflects the pressure on the liquid; and an elastomeric bladder sealed around the entrance to the neck so as to isolate the liquid from the fluid within the reservoir and exert pressure upon the liquid in response to pressure from the fluid to actuate the gauge, the bladder in shape of a bubble disposed within the neck at rest and extending further within the neck under pressure.

9. A device according to claim 6 and wherein the housing contains a timer.

* * * * *

UNITED STATES PATENT AND TRADEMARK OFFICE
CERTIFICATE OF CORRECTION

PATENT NO. : 5,284,480
DATED : February 8, 1994
INVENTOR(S) : William M. Porter, Susan L. Stout It is certified that error appears in the above-indentified patent and that said Letters Patent is hereby corrected as shown below:

Col. 8, line 20, "7" should be --6--.

Signed and Sealed this

Nineteenth Day of July, 1994

Attest:

BRUCE LEHMAN

*Attesting Officer*        *Commissioner of Patents and Trademarks*